United States Patent [19]

Quinn et al.

[11] Patent Number: 5,037,387
[45] Date of Patent: Aug. 6, 1991

[54] METHOD OF POSITIONING AN ENTERAL FEEDING TUBE WITHIN A PATIENT'S BODY

[75] Inventors: David G. Quinn, Grayslake; Erik Andersen, Vernon Hills, both of Ill.

[73] Assignee: Corpak, Inc., Wheeling, Ill.

[21] Appl. No.: 469,218

[22] Filed: Jan. 24, 1990

[51] Int. Cl.⁵ .............................. A61M 31/00
[52] U.S. Cl. ................................ 604/51; 604/270
[58] Field of Search .............. 604/51, 93, 264, 266, 604/267, 270, 280

[56] References Cited

U.S. PATENT DOCUMENTS

| | | | |
|---|---|---|---|
| 1,736,182 | 11/1929 | Wilkins | 604/270 |
| 1,899,781 | 2/1933 | Twiss | 604/270 |
| 4,594,074 | 6/1986 | Andersen et al. | 604/270 |
| 4,613,323 | 9/1986 | Norton et al. | 604/43 |
| 4,692,152 | 9/1987 | Emde | 604/164 |
| 4,778,455 | 10/1988 | Kousai et al. | 604/270 |
| 4,781,704 | 11/1988 | Potter | 604/270 |
| 4,854,330 | 8/1989 | Evans, III et al. | 128/772 |

FOREIGN PATENT DOCUMENTS 0591963  7/1925  France ................ 604/270

Primary Examiner—John D. Yasko
Assistant Examiner—Adam J. Cermak
Attorney, Agent, or Firm—Wallenstein, Wagner & Hattis

[57] ABSTRACT

An improved enteral feeding tube (10) having a distal (12) and a proximal end (14). The tube (10) has a generally circular cross-section, and includes an attachment (22) made of flexible polyurethane that is adhered to the distal end (12) of the enteral feeding tube (10). The attachment (22) comprises a generally rigid stem portion (24) extending from the distal end (12) of the enteral tube (10), and along an axis generally parallel to the axis of the feeding tube. The attachment (22) further comprises a spherical tip (28) at one end of the rigid stem portion (24).

4 Claims, 1 Drawing Sheet

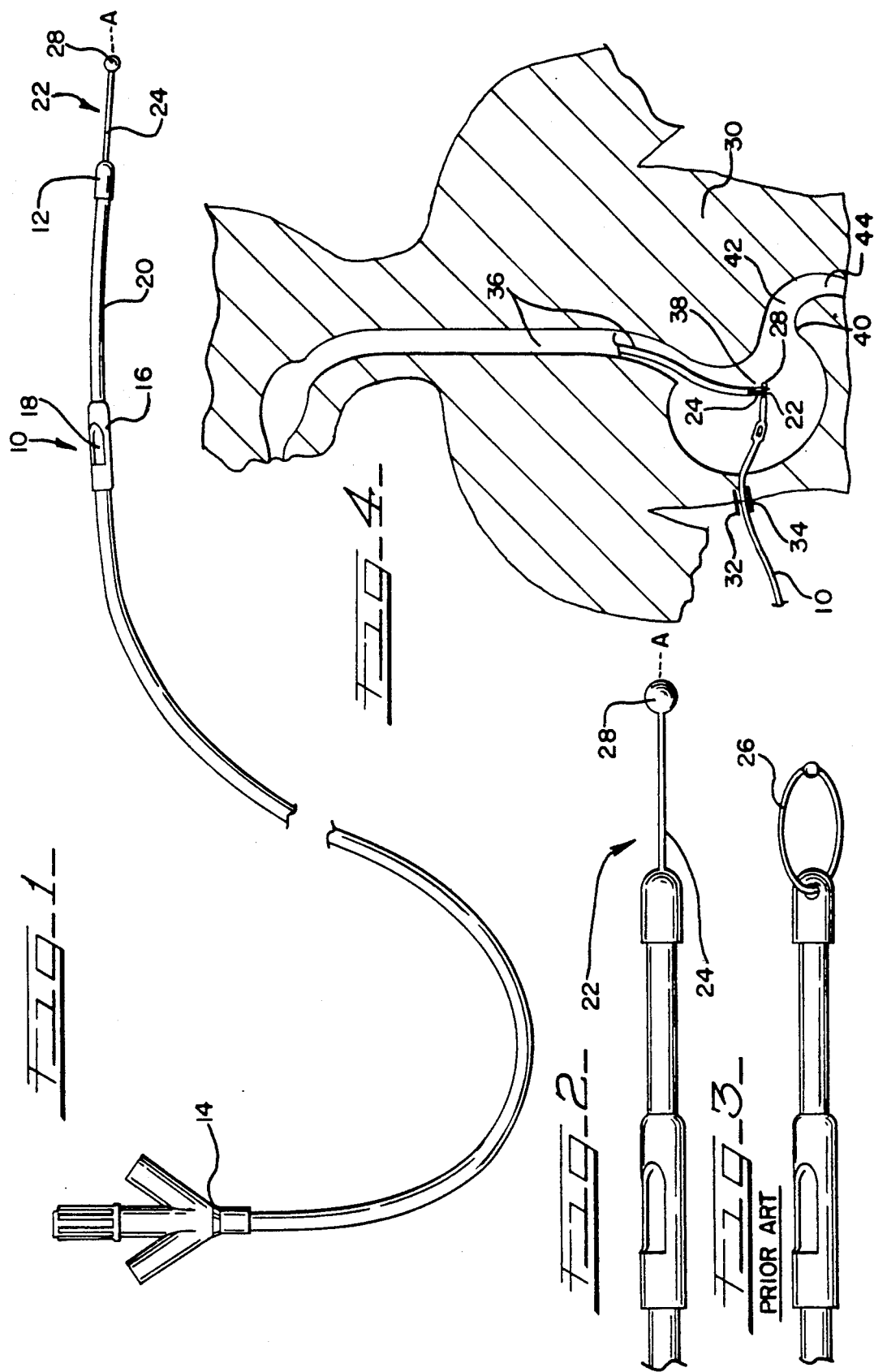

METHOD OF POSITIONING AN ENTERAL FEEDING TUBE WITHIN A PATIENT'S BODY

TECHNICAL FIELD

The invention relates to the field of catheters, and especially those used in enteral feeding. More particularly, the invention relates to improvements in enteric or enteral feeding tubes, and to their improved placement within the body of a patient.

BACKGROUND OF THE INVENTION

Enteral feeding tubes are well-known in the art. One such enteral feeding tube is disclosed, for example, in U.S. Pat. No. 4,594,074, issued to Andersen et al. on June 10, 1986, and assigned to the predecessor of the assignee of the present invention.

Percutaneous access through a surgically formed gastrostomy permits direct placement of an enteral feeding tube within the stomach. The feeding tube may be inserted through a conventional tube in an ostomy, for example, a percutaneous endoscopic gastrostomy (PEG) tube. Correct placement of an enteral feeding tube within the stomach or small intestine is currently facilitated by an attachment adhered to the distal end of the enteral feeding tube. This enteral feeding tube attachment includes a small hole through which a suture is looped.

After the enteral feeding tube has been placed through the ostomy and into the stomach, the loop of this suture aids in proper positioning of the distal end of the feeding tube within portions of the gastrointestinal tract beyond the pylorus valve. Particularly, the loop is grasped by endoscopic forceps. By manipulation of the forceps, the loop and the distal end of the enteral feeding tube are properly positioned within either the duodenum or the jejunum.

There are, however, certain drawbacks to this prior art, loop-containing attachment. First, the suture is intended to lead and extend in a forward direction from the distal end of the enteral feeding tube. The suture is, however, made of a non-rigid fabric. For this reason, as the enteral feeding tube is inserted through the PEG tube or cannula within the ostomy, the suture has a tendency to trail the feeding tube. This tendency causes the suture to become reversed, and to "double-over" the sides of the feeding tube. The suture thus becomes lodged between the enteral feeding tube and the PEG tube. As a result, the effective outer diameter of the feeding tube is increased. Because the actual outer diameter of the enteral feeding tube is designed to be only slightly smaller than the inner diameter of the PEG tube, this "doubling-over" of the suture inhibits the free movement of the enteral feeding tube through the PEG tube.

Yet another problem arises when the feeding tube has been inserted within the body of the patient. As discussed above, the loop of the suture is grasped by a pair of endoscopic forceps. As it is moved through the body, the suture loop absorbs and tends to become wetted by various body fluids. When the enteral feeding tube is properly positioned within the duodenum or jejunum and the endoscopic forceps are opened to release the wetted suture, that suture may nevertheless stick to the forceps. As a result, the suture and the enteral feeding tube to which it is attached may follow the forceps while the forceps are being withdrawn from the body cavities. In this manner, the enteral feeding tube may be moved from its intended position.

As a result of these shortcomings of the prior art, it was deemed desirable to design a modified attachment for enabling precise placement of an enteral feeding tube within a body cavity.

SUMMARY OF THE INVENTION

The invention is an enteral feeding tube having a unique distal end extension or attachment and to the method of insertion thereof into the patient's body. The attachment may be integrally molded with or secured to a conventional enteral tube. The tube is of the type generally known in the prior art, and has a conventional, generally circular cross-section. The attachment comprises a generally rigid stem portion. This stem portion extends from the distal end portion of the enteral tube. It extends along an axis generally parallel to the axis of that tube. An enlarged tip, preferably a spherical tip, is formed at one end of the rigid stem portion.

The attachment is preferably made of a flexible polyurethane. As indicated above, the attachment may be either adhered to or integrally molded to the distal end of the feeding tube.

An object of the present invention is to provide an improved method of insertion of inserting an enternal feeding tube into a patient's body using an improved enteral feeding tube which facilitates the proper entry and movement of that tube through yet another tube in an ostomy, such as a cannula or a PEG tube. Another object of the invention is to provide an improved method using an improved enteral feeding tube which ensures proper placement of that tube within the patient's body. Still another object of the present invention is to provide a method of ental tube insertion and positioning which maintains a relatively low risk of puncturing organs as that tube is moved through the body.

BRIEF DESCRIPTION OF THE DRAWINGS

FIG. 1 is perspective view of the improved enteral feeding tube used in the present method invention, and including a unique attachment secured to that feeding tube;

FIG. 2 is a perspective view of the attachment shown in FIG. 1;

FIG. 3 is a perspective view of the distal end of an enteral feeding tube in accordance with the prior art, and showing the looped suture used in such prior art devices; and FIG. 4 is an illustrative diagram showing the present method invention involving the insertion and positioning of the enteral feeding tube and attachment shown in FIGS. 1-3 by the gripping and movement thereof by a pair of endoscopic forceps.

DETAILED DESCRIPTION OF THE PREFERRED EMBODIMENT

Referring now to the drawings, the unique ental feeding tube used in the present method invention is shown in FIG. 1, and in FIG. 2.

The improved enteral feeding tube 10 there shown has a distal end 12 and a proximal end 14 of generally circular cross-section. In other respects, this tube 10 is similar to that described in U.S. Pat. No. 4,594,074, issued to Andersen et al. on June 10, 1986. Thus, it includes a bolus 16 adjacent to the distal end 12. This bolus 16 includes an opening 18 having a generally ellipsoidal edge configuration and defining a tube outlet. The tube 10 includes a weighted end section 20 between the bolus 16 and the distal end 12. This weighted end section 20 is weighted with metal discs or any other weighing means conventional in the art.

The enteral feeding tube 10 of the present invention includes an attachment 22 which replaces an attachment used in prior art enteral tubes. This attachment 22 is shown secured to an enteral tube in FIG. 1, and is also shown alone in FIG. 2.

For reasons that will become apparent, the attachment 22 should be both somewhat rigid and yet flexible. Particularly, the attachment 22 should be sufficiently rigid so that its stem portion 24 will remain upright when the attachment is pointed upwardly. The attachment 22 should be sufficiently flexible so as to not harm tissue when moved within the body of a patient, and sufficiently flexible so that forceps may bend that stem portion 24. Thus, an ideal and preferred material for the attachment 22 is polyurethane.

Because polyurethane is the same material as that preferred for enteral feeding tubes of the prior art, the attachment 22 may be secured to the distal end 12 of the enteral feeding tube 10 with tetrahydrofurane (THF). Particularly, the distal end 12 of the enteral feeding tube 10 is wetted by dipping into either pure THF or a solution of 93% THF and 7% polyurethane. Adhesion takes place rapidly after the attachment 22 is slipped over the wetted portion of the tube 10.

Although the above-described embodiment contemplates a discrete and separate attachment 22 which is secured by tetrahydrofurane to the enteral feeding tube 10, it will be understood by those skilled in the art that the attachment 22 may instead be integrally molded, i.e., as one piece, together with the tube 10.

Referring now to FIG. 2, the attachment 22 itself includes a generally rigid stem portion 24. Because this stem portion 24 is made of polyurethane, it is sufficiently rigid to avoid the tendency of prior art sutures 26 (FIG. 3) to become reversed, or "doubled-over," the sides of the feeding tube as that tube is inserted through yet another tube, such as a PEG tube or cannula, extending from an ostomy. Polyurethane also has sufficient flexibility so that the endoscopist may grasp the stem portion 24 with the endoscopic forceps and twist or bend it as desired as the enteral feeding tube 10 is moved from the stomach and into the duodenum or jejunum.

In the present preferred embodiment, this stem portion 24 has a circular cross-section, a diameter of about one (1) millimeter, and a length of approximately eighteen (18) millimeters. The stem portion 24 extends from the distal end 12 of the enteral feeding tube 10, and along an axis A-A that is generally parallel to the axis of a straightened, extended feeding tube 10.

The attachment 22 also comprises a generally enlarged tip, preferably a spherical tip 28. In this embodiment, this tip is integrally molded to one end of the rigid stem portion 24. The tip 28 is made generally spherical to lessen the danger that the attachment 22, and particularly its stem portion 24, punctures the tissue when the improved tube 10 with its leading attachment 22 is moved through the gastrointestinal tract. However, it will be understood by those skilled in the art that any shape which has the effect of distributing force over an enlarged area will be generally suitable for use as a tip 28. More particularly, any edgeless shape will be suitable for use as a tip in the present invention. In the present embodiment shown in FIGS. 1 and 2, the spherical tip 28 has a diameter of approximately four (4) millimeters.

Referring now to FIG. 4, the improved enteral feeding tube 10 used in the present method invention is shown in place within a patient 30. The enteral feeding tube 10 is shown passing through a cannula 32 in the ostomy or stoma 34. However, a PEG tube or any other comparable device which parts the tissue of the stoma 34 may be used in lieu of the cannula 32. It is also contemplated that a sufficiently narrow enteral feeding tube in accordance with this invention could be placed into the stomach through an endoscope.

Also shown in FIG. 4 are an endoscope 36 positioned in the stomach of the patient 30. Through the use of the endoscope 36, the endoscopist may view the attachment 22, including the stem portion 24 and its tip 28. Endoscopic forceps 38 are positioned in the stomach through the endoscope 36, and the endoscopist grips the stem portion 24 of the attachment 22 with the forceps 38.

The endoscopist may now move the attachment 22 and the tube 10 through the pylorus valve 40 of the stomach and into position in the duodenum 42 or the jejunum 44. The endoscopist is free to twist the flexible stem portion 24 to facilitate this positioning. In addition to its role in lowering the chances of puncturing the intestine while the tube 10 is moved into position, the tip 28 also prevents the forceps from slipping off of the leading end of the stem portion 24 during the pulling or tugging motions of such positioning.

After the tube 10 has been properly positioned within the duodenum 42 or jejunum 44, the endoscopist releases the forceps 38 from their gripping engagement of the stem portion 24. Even if that stem portion 24 is wetted by body fluids, the forceps 38 will not stick to that stem portion 24 upon release. Accordingly, the enteral feeding tube 10 will not move away from its proper position as the forceps are removed from the duodenum 42 or jejunum 44.

This embodiment describes the use of endoscopic forceps to position the enteral feeding tube. It will be apparent to those skilled in the art that the snare on an endoscope may also be used. This snare, when opened to a sufficiently large diameter, could be moved over the tip 28 and onto the stem portion 24. The snare could then be decreased to a diameter less than that of the tip 28. In this way, the snare would not slip off of the attachment 22 during movement of the tube 10 into its proper location within the duodenum or jejunum. After the tube 10 was properly positioned, the snare's diameter could again be increased, permitting the endoscopist to move the snare over the tip 28 of and away from the attachment 22.

Accordingly, it may be seen that the attachment 22 used in the present method invention, and particularly its relatively rigid but flexible stem portion 24, facilitates entry of the enteral feeding tube 10 through yet another tube in an ostomy, such as a cannula 32 or a PEG tube. In particular, the unique stem portion avoids the "doubling-over" of prior art sutures which effectively increases the outer diameter of the feeding tube 10. The unique attachment design also ensures proper placement of the enteral feeding tube 10 within the body of a patient 30 by providing a stem portion 24 that is made of a material which will, even when wetted with body fluids, readily release away from the forceps 38 which position that tube 10. The unique attachment design provides all of these advantages in the method of the present invention while still maintaining a relatively low risk of puncturing organs as the feeding tube 10 is moved through the body.

While the specific embodiments have been illustrated and described, numerous modifications come to mind without markedly departing from the spirit of the invention. The scope of protection is thus only intended to be limited by the scope of the accompanying claims.

What we claim is:

1. A method of endoscopic placement of an enteral feeding tube within a gastrointestinal tract, said enteral feeding tube having a distal and a proximal end, a generally circular cross-section, an attachment comprising a generally rigid stem portion extending from said distal end of said enteral tube, and along an axis generally parallel to the axis of said feeding tube, and an enlarged non-soluble tip at one end of said rigid stem portion, said method comprising the steps of:
   a. positioning said endoscope within the stomach of a patient;
   b. grippingly engaging said stem portion of said attachment with endoscopic forceps;
   c. moving said attachment and said tube through and into position within said gastrointestinal tract, whereby said tip prevents said forceps from slipping off of the leading end of said stem portion during such positioning; and
   d. releasing said forceps from their gripping engagement with said stem portion.

2. A method of endoscopic placement of an enteral feeding tube within a gastrointestinal tract, said enteral feeding tube having a distal and a proximal end, a generally circular cross-section, an attachment comprising a generally rigid stem portion extending from said distal end of said enteral tube, and along an axis generally parallel to the axis of said feeding tube, and an enlarged non-soluble tip at one end of said rigid stem portion, said method comprising the steps of:
   a. positioning said endoscope within the stomach of a patient;
   b. moving an endoscopic snare over said tip;
   c. grippingly engaging said stem portion of said attachment by decreasing the diameter of said endoscopic snare to a diameter less than that of said tip;
   d. moving said attachment and said tube through and into position within said gastrointestinal tract, whereby said tip prevents said endoscopic snare from slipping off of the leading end of said stem portion during such positioning; and
   e. releasing said endoscopic snare from its engagement with said stem portion by increasing the diameter of said snare and moving said snare over said tip and away from said attachment.

3. The method of claims 1 or 2 wherein said enteral feeding tube is inserted within the patient's stomach through another tube inserted into the patient's abdomen.

4. The method of claim 3 wherein said endoscope is inserted into the patient's stomach through the passageway which leads from the patient's mouth to the stomach.

* * * * *